US012752122B2

(12) United States Patent
Horan et al.

(10) Patent No.: US 12,752,122 B2
(45) Date of Patent: Oct. 6, 2026

(54) DYNAMIC SWITCHING BETWEEN CRT AND MSP

(71) Applicant: Cardiac Pacemakers, Inc., St. Paul, MN (US)

(72) Inventors: Sean Thomas Horan, Maplewood, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 350 days.

(21) Appl. No.: 18/528,985

(22) Filed: Dec. 5, 2023

(65) Prior Publication Data

US 2024/0181263 A1 Jun. 6, 2024

Related U.S. Application Data

(60) Provisional application No. 63/430,243, filed on Dec. 5, 2022.

(51) Int. Cl.

*A61N 1/36* (2006.01)
*A61N 1/365* (2006.01)
*A61N 1/368* (2006.01)

(52) U.S. Cl.

CPC ....... *A61N 1/3688* (2013.01); *A61N 1/36521* (2013.01); *A61N 1/36585* (2013.01); *A61N 1/36842* (2017.08); *A61N 1/36843* (2017.08)

(58) Field of Classification Search

CPC .............. A61N 1/3688; A61N 1/36521; A61N 1/36585; A61N 1/36842; A61N 1/36843; A61N 1/3627

See application file for complete search history.

(56) References Cited

U.S. PATENT DOCUMENTS

| | | | |
|---|---|---|---|
| 7,115,096 B2 | 10/2006 | Siejko et al. | |
| 7,853,327 B2 | 12/2010 | Patangay et al. | |
| 2019/0083789 A1* | 3/2019 | Thakur | A61B 7/00 |
| 2019/0275338 A1* | 9/2019 | An | A61N 1/3627 |
| 2020/0188674 A1 | 6/2020 | An et al. | |
| 2022/0161035 A1 | 5/2022 | Stegemann et al. | |

OTHER PUBLICATIONS

"Cardiac Resynchronization Therapy", Brochure, www.bostonscientific.com, © 2014 Boston Scientific Corporation or its affiliates. CRT-P 356430-007 EN USA Apr. 2014, 96 pages.

"Cardiac Resynchronization Therapy Defibrillator", Brochure, www.bostonscientific.com, © 2017 Boston Scientific Corporation or its affiliates. CRT-D 356965-008 EN USA Mar. 2017, 130 pages.

(Continued)

*Primary Examiner* — Rex R Holmes

(74) *Attorney, Agent, or Firm* — Nelson Mullins Riley & Scarborough LLP

(57) ABSTRACT

Systems and methods are disclosed to control transition of a stimulation circuit configured to generate first and second stimulation signals in different respective first and second stimulation modes between the different respective first and second stimulation modes using a patient metric determined using received physiologic information of the patient including at least one of thoracic impedance information or respiration information from a first time period.

20 Claims, 8 Drawing Sheets

(56) References Cited

OTHER PUBLICATIONS

Saba, Samir, et al., "Usefulness of Multisite Ventricular Pacing in Nonresponders to Cardiac Resynchronization Therapy", Am J Cardiol 2022;164:86-92. doi: 10.1016/j.amjcard.2021.10.027. Epub Nov. 20, 2021. PMID: 34815062.

International Preliminary Report on Patentability received for PCT Patent Application No. PCT/US2023/082425, mailed on Jun. 19, 2025, 9 pages.

International Search Report and Written Opinion received for PCT Patent Application No. PCT/US2023/082425, mailed on Mar. 28, 2024, 11 pages.

Samir et al., "Usefulness of Multisite Ventricular Pacing in Nonresponders to Cardiac Resynchronization Therapy", American Journal of Cardiology, Cahners Publishing Co., Newton, MA, US, vol. 164, Nov. 20, 2021, pp. 86-92.

* cited by examiner

DYNAMIC SWITCHING BETWEEN CRT AND MSP

CLAIM OF PRIORITY

This application claims the benefit of U.S. Provisional Application No. 63/430,243, filed on Dec. 5, 2022, which is hereby incorporated by reference in its entirety.

TECHNICAL FIELD

This document relates generally to medical devices and more particularly to dynamic switching between cardiac resynchronization therapy (CRT) and multi-site pacing (MSP) for therapy delivery using physiologic information of a patient.

BACKGROUND

Heart failure (HF) is a reduction in the ability of the heart to deliver enough blood to meet bodily needs. Heart failure patients commonly have enlarged hearts with weakened cardiac muscles, resulting in reduced contractility and poor cardiac output. Signs of heart failure include pulmonary congestion, edema, difficulty breathing, etc. Heart failure is often a chronic condition, but can also occur suddenly, affecting the left, right, or both sides of the heart. Causes of heart failure include coronary artery disease, myocardial infarction, high blood pressure, atrial fibrillation, valvular heart disease, alcoholism, infection, cardiomyopathy, or one or more other conditions leading to a decreased pumping efficiency of the heart.

Medical devices, including ambulatory, implantable, subcutaneous, wearable, or one or more other medical devices, etc., can monitor, detect, or treat various conditions including heart failure, atrial fibrillation, etc. Medical devices can include sensors to sense physiologic information from a patient and one or more circuits to detect one or more physiologic events using the sensed physiologic information or transmit sensed physiologic information or detected physiologic events to one or more remote devices. Additionally, medical devices can be configured to provide electrical stimulation or one or more other therapies or treatments to the patient, such as to improve cardiac function, etc.

Frequent patient monitoring can provide early detection of worsening patient condition, including worsening heart failure or atrial fibrillation. Accurate identification of patients or groups of patients at an elevated risk of future adverse events may control mode or feature selection or resource management of one or more medical devices, control notifications or messages in connected systems to various users associated with a specific patient or group of patients, organize or schedule physician or patient contact or treatment, or prevent or reduce patient hospitalization. Correctly identifying and safely managing patient risk of worsening condition may avoid unnecessary medical interventions, extend the usable life of medical devices, and reduce healthcare costs. In addition, in situations where different operating modes, features, or therapies are available, correctly monitoring, detecting, and identifying patient status, including improving or worsening patient condition, and modifying one or more medical device functions accordingly, can improve medical device efficiency, such as by reducing unnecessary resource consumption, thereby extending the usable life of the ambulatory medical device.

SUMMARY

Systems and methods are disclosed to control transition of a stimulation circuit configured to generate first and second stimulation signals in different respective first and second stimulation modes between the different respective first and second stimulation modes using a patient metric determined using received physiologic information of the patient including at least one of thoracic impedance information or respiration information from a first time period.

An example (e.g., "Example 1") of subject matter (e.g., a medical device system) may comprise a stimulation circuit configured to generate first and second stimulation signals in different respective first and second stimulation modes, the first and second stimulation signals configured to be provided to a heart of a patient and a signal receiver circuit configured to receive physiologic information of the patient, including at least one of thoracic impedance information or respiration information and an assessment circuit configured to control transition of the stimulation circuit between the first and second stimulation modes, including to determine a patient metric using the received physiologic information from a first time period and control transition of the stimulation circuit between the first stimulation mode and the second stimulation mode based on the determined patient metric.

In Example 2, the subject matter of Example 1 may optionally be configured such that the first time period occurs while the stimulation circuit is in the first stimulation mode and to control transition between the first and second stimulation modes comprises to control transition from the first stimulation mode to the second stimulation mode based on the determined patient metric.

In Example 3, the subject matter of any one or more of Examples 1-2 may optionally be configured such that the assessment circuit is configured to control implementation of the first stimulation mode at a first time, wherein the first time period occurs after the first time and to control transition of the stimulation circuit from the first stimulation mode to the second stimulation mode comprises at a second time after the first time period.

In Example 4, the subject matter of any one or more of Examples 1-3 may optionally be configured such that to control transition of the stimulation circuit from the first stimulation mode to the second stimulation mode at the second time comprises to compare the determined patient metric to a threshold, transition the stimulation circuit from the first stimulation mode to the second stimulation mode if the determined patient metric exceeds a first threshold, and retain the stimulation circuit in the first stimulation mode if the determined patient metric does not exceed the first threshold.

In Example 5, the subject matter of any one or more of Examples 1~4 may optionally be configured such that the first stimulation mode comprises a cardiac resynchronization therapy (CRT) mode configured to generate stimulation signals to be delivered to at least one of a single electrode in a first chamber of the heart or a single electrode in a second chamber of the heart and the second stimulation mode comprises a multi-site pacing (MSP) mode configured to generate stimulation signals to be delivered to multiple electrodes in one of the first or second chambers of the heart.

In Example 6, the subject matter of any one or more of Examples 1-5 may optionally be configured such that the CRT mode is configured to generate biventricular pacing signals to be delivered to a single electrode in each of a right and a left ventricle of the heart and the MSP therapy mode is configured to generate stimulation signals to be delivered to multiple electrodes in the left ventricle of the heart.

In Example 7, the subject matter of any one or more of Examples 1-6 may optionally be configured such that the first time period occurs while the stimulation circuit is in the second stimulation mode and to control transition between the first and second stimulation modes comprises to control transition from the second stimulation mode to the first stimulation mode based on the determined patient metric.

In Example 8, the subject matter of any one or more of Examples 1-7 may optionally be configured such that the thoracic impedance information includes intrathoracic impedance (ITTI) information and the respiration information includes rapid shallow breathing index (RSBI) information.

In Example 9, the subject matter of any one or more of Examples 1-8 may optionally be configured such that the assessment circuit is configured to determine the patient metric as a function of the ITTI information and the RSBI information.

In Example 10, the subject matter of any one or more of Examples 1-9 may optionally be configured such that the respiration information includes a measure of tidal volume (TV).

An example (e.g., "Example 11") of subject matter (e.g., a method) may comprise generating, using a stimulation circuit, first and second stimulation signals in different respective first and second stimulation modes, the first and second stimulation signals configured to be provided to a heart of a patient, receiving, using a signal receiver circuit, physiologic information of the patient, including at least one of thoracic impedance information or respiration information and controlling, using an assessment circuit, transition of the stimulation circuit between the first and second stimulation modes, including determining a patient metric using the received physiologic information from a first time period and controlling transition of the stimulation circuit between the first stimulation mode and the second stimulation mode based on the determined patient metric.

In Example 12, the subject matter of any one or more of Examples 1-11 may optionally be configured such that the first time period occurs while the stimulation circuit is in the first stimulation mode and controlling transition between the first and second stimulation modes comprises controlling transition from the first stimulation mode to the second stimulation mode based on the determined patient metric.

In Example 13, the subject matter of any one or more of Examples 1-12 may optionally include controlling control implementation of the first stimulation mode at a first time, wherein the first time period occurs after the first time, wherein controlling transition of the stimulation circuit from the first stimulation mode to the second stimulation mode comprises at a second time after the first time period.

In Example 14, the subject matter of any one or more of Examples 1-13 may optionally be configured such that controlling transition of the stimulation circuit from the first stimulation mode to the second stimulation mode at the second time comprises comparing the determined patient metric to a threshold, transitioning the stimulation circuit from the first stimulation mode to the second stimulation mode if the determined patient metric exceeds a first threshold, and retaining the stimulation circuit in the first stimulation mode if the determined patient metric does not exceed the first threshold.

In Example 15, the subject matter of any one or more of Examples 1-14 may optionally be configured such that the first stimulation mode comprises a cardiac resynchronization therapy (CRT) mode configured to generate stimulation signals to be delivered to at least one of a single electrode in a first chamber of the heart or a single electrode in a second chamber of the heart and the second stimulation mode comprises a multi-site pacing (MSP) mode configured to generate stimulation signals to be delivered to multiple electrodes in one of the first or second chambers of the heart.

In Example 16, the subject matter of any one or more of Examples 1-15 may optionally be configured such that the CRT mode is configured to generate biventricular pacing signals to be delivered to a single electrode in each of a right and a left ventricle of the heart and the MSP therapy mode is configured to generate stimulation signals to be delivered to multiple electrodes in the left ventricle of the heart.

In Example 17, the subject matter of any one or more of Examples 1-16 may optionally be configured such that the first time period occurs while the stimulation circuit is in the second stimulation mode and controlling transition between the first and second stimulation modes comprises controlling transition from the second stimulation mode to the first stimulation mode based on the determined patient metric.

In Example 18, the subject matter of any one or more of Examples 1-17 may optionally be configured such that the thoracic impedance information includes intrathoracic impedance (ITTI) information and the respiration information includes rapid shallow breathing index (RSBI) information.

In Example 19, the subject matter of any one or more of Examples 1-18 may optionally be configured such that determining the patient metric comprises as a function of the ITTI information and the RSBI information.

In Example 20, the subject matter of any one or more of Examples 1-19 may optionally be configured such that the respiration information includes a measure of tidal volume (TV).

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
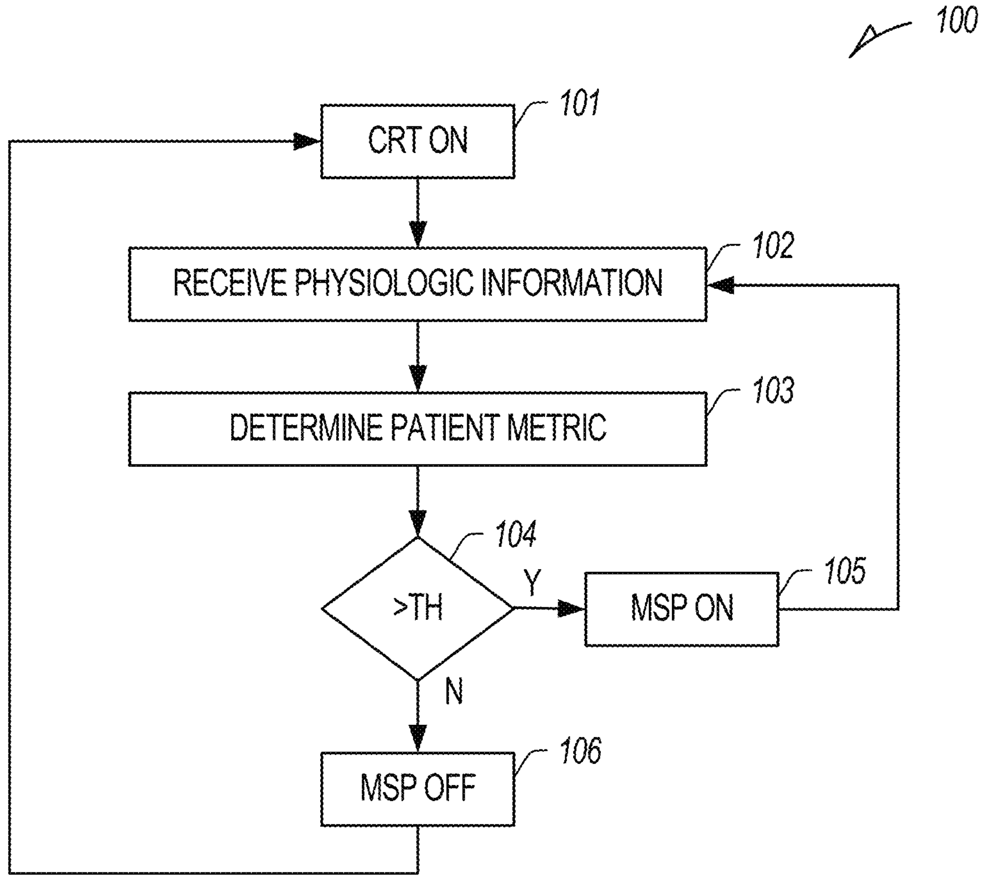
FIG. 1 illustrates an example process to control transition between therapy modes using a determined patient parameter.

Medical devices can be implanted in a patient or otherwise positioned on or about the patient to monitor patient physiologic information, such as heart sound information, respiration information (e.g., respiration rate (RR), tidal volume (TV), rapid shallow breathing index (RSBI), etc.), impedance information (e.g., intrathoracic impedance (ITTI)), pressure information, cardiac electrical information (e.g., heart rate), physical activity information, or other physiologic information or one or more other physiologic parameters of the patient, or to provide electrical stimulation or one or more other therapies or treatments to optimize or control contractions of a heart of the patient. For example, the medical device can include one or more implantable medical devices (IMDs), such as cardiac resynchronization therapy (CRT) devices, etc., configured to receive cardiac electrical information from, and in certain examples, provide electrical stimulation to, one or more electrodes located within, on, or proximate to the heart, such as coupled to one or more leads and located in one or more chambers of the heart, within the vasculature of the heart near one or more chambers, or otherwise attached to or in contact with the heart.

Stimulation signals can be generated and provided one or more chambers of the heart (e.g., frequently two or more of the right ventricle (RV), the left ventricle (LV) (e.g., commonly through the cardiac vasculature), or the right atrium (RA), etc.) to improve cardiac function, such as improving coordination of contractions between different chambers of the heart (e.g., the right ventricle and the left ventricle, the right atrium and the right ventricle, etc.) or otherwise improving cardiac output or efficiency. Different therapy modes can provide different therapies, however, with different power and resource requirements and varying effectiveness for different respective patients. A variety of therapy modalities are available to patients, but not all patients receive the optimal medical device, therapy mode, or therapy settings.

The present inventors have recognized, among other things, systems and methods to determine which of multiple therapies may be more effective for a respective patient using physiologic information from the respective patient, in certain examples, before providing one or more of the therapy modes, or before transitioning from a first therapy mode to a second therapy mode.

Conventional CRT includes generating and applying stimulation signals to one or more chambers of the heart to improve coordination of contraction of the different chambers or to otherwise improve cardiac output or efficiency. CRT can include biventricular pacing of the right and left ventricles of the heart, but also can include single-chamber pacing (e.g., right ventricle pacing, left ventricle pacing, etc.), sensing or pacing in one or more other chambers or combinations of chambers, etc. The timing of stimulation signals in the cardiac cycle or with respect to one or more cardiac events often varies depending on a number of factors, including placement of the lead or electrodes, propagation of the stimulation signals through the tissue, stimulation amplitudes, etc.

In contrast, multi-site pacing (MSP) (or multisite pacing) therapy commonly refers to applying one or more stimulation signals to multiple electrodes (e.g., two or more) in or proximate to a first chamber (e.g., commonly the left ventricle, but also in certain examples the right ventricle, the right atrium, or combinations thereof) for a single cardiac cycle. The same or different stimulation signals can be applied to different electrodes in or proximate to the first chamber during MSP therapy at the same time, at different times (e.g., with a delay), or in combinations thereof for a single cardiac cycle.

Certain heart failure patients respond to (e.g., benefit from) MSP therapy that do not respond to CRT. Other patients don't respond to either. Pacing therapies are frequently evaluated, such as to ensure that the applied pacing therapy is providing some benefit to the patient, to determine whether or not the pacing therapy should be adjusted, or to determine if the pacing therapy should be transitioned. For example, a study by Samir Saba et al. titled "Usefulness of Multisite Ventricular Pacing in Nonresponders to Cardiac Resynchronization Therapy" in The American Journal of Cardiology, Feb. 1, 2022 (herein "the Saba study") found that 25% to 40% of heart failure patients with myocardial dysfunction did not respond to conventional CRT by evaluation at 6 months post implant, but also found that over half (51.3%) of non-responders to CRT at 6 months did subsequently respond to 6 months of MSP therapy in the left ventricle by evaluation at 12 months post implant. Evaluation in the Saba study was based on assessment of patient mortality, the occurrence of heart failure events, global patient assessment, and general NYHA heart failure classification.

Although the transition from CRT to MSP therapy in the left ventricle was substantially complication free physiologically, the switch to MSP therapy from conventional CRT can provide at least some cardiac stress, but also requires additional resources from the implantable medical device. In certain estimates, implementing MSP therapy in a device capable of MSP therapy and CRT reduces the estimated life of the device by 11-13%. Even a single six-month evaluation of MSP therapy on an IMD can impact the usable life of the IMD by a relatively substantial and often unnecessary amount.

The present inventors have recognized, among other things, that certain physiologic information sensed from the patient in one or more time periods can be used to determine one or more MSP response metrics, and that such one or more determined MSP response metrics can be used to provide an alert or notification or otherwise control transition between different medical device modes (e.g., a first stimulation mode, a second stimulation mode, etc.) mode, including, in certain examples, to: (1) control transition of non-MSP therapy mode to an MSP therapy mode; (2) control transition of the MSP therapy mode to a non-MSP therapy mode; or (3) enable or disable the MSP therapy mode.

Moreover, the present inventors have recognized that specific physiologic information sensed from the patient subsequent to implementing a stimulation mode can be used to determine an MSP response metric configured to determine an indication of a predicted patient response to the stimulation mode, such that, in certain examples, a stimulation mode can be evaluated without entering the stimulation mode. In particular, the present inventors have recognized specific physiologic information or combinations of physiologic information can be determined to evaluate a stimulation mode or to predict a positive patient response to a particular stimulation mode, such as using a response to another stimulation mode, etc. In an example, physiologic information sensed or detected during a CRT mode can be used to determine if a patient is likely to respond to (e.g., benefit from) an MSP therapy mode before the MSP therapy mode is implemented or enabled.

In an example, the present inventors have recognized, among other things, that one or more of impedance information (e.g., ITTI) and respiration information (e.g., RSBI), or a combination thereof, over one or more time periods (e.g., 60 day time periods, 150 day time periods, etc.) can be used to determine an indication that a patient will respond to an MSP therapy mode before the MSP therapy mode is implemented or enabled. An example, equation (1), is provided below.

$$p(\mathrm{MSP}_{response}) \propto (\alpha \times \mathrm{ITTI}) + (\beta \times \mathrm{RSBI}) \quad (1)$$

In equation (1), $p(\mathrm{MSP}_{response})$ is a patient metric (e.g., an MSP response metric), ITTI is a measure of patient intrathoracic impedance, RSBI is a measure of patient respiration rate (RR) or frequency to a measure of tidal volume (TV) (e.g., RR/TV, etc.), and $\alpha$ and $\beta$ are variables. In other examples, the patient metric can be determined using only one of ITTI or RSBI information, or as different functions of one or more of such physiologic parameters in combination with one or more other physiologic parameters. Using physiologic information from a time period in a therapy mode prior to implementing an MSP therapy mode (e.g., from within a conventional CRT mode), the present inventors were able to determine a positive MSP response using equation (1) and a threshold (TH) with an area under the ROC curve of 0.8309 with a 95% confidence interval. Once in the MSP therapy mode, the present inventors were able to determine a positive MSP response using equation (1) and a threshold (TH) with an area under the ROC curve of 0.78527 with a 95% confidence interval. Such determinations are highly sensitive.

FIG. 1 illustrates an example process 100 to control transition between therapy modes using a determined patient parameter. Based on training data, the patient metric can be determined with a 50% true positive rate and a 0% true negative rate. In certain examples, a highly sensitive determination can be required, such as by adjusting equation (1) or one or more thresholds, prior to transitioning to the MSP therapy mode to conserve medical device resources and avoid unnecessary cardiac stress associated with the transition.

At step 101, a CRT mode can be implemented, for example, at a first time, in certain examples. Although described herein as starting with implementation of the CRT mode, in other examples, the process can begin with one or more other therapy modes, or from a monitoring mode without therapy. In certain examples, a stimulation circuit can generate and provide one or more stimulation signals in one or more stimulation modes, and an assessment circuit can be configured to control the stimulation circuit, such as to adjust one or more parameters or transition between different therapy modes, etc.

At step 102, physiologic information can be received from one or more sensors, such as using a signal receiver circuit. The received physiologic information can include, but is not limited to, patient ITTI information, patient RSBI information, or one or more other types of patient information, such as described herein.

At step 103, a patient metric, such as one or more MSP response metrics, can be determined based on the received physiologic information, such as described with respect to equation (1) or otherwise described herein, in certain examples, using the assessment circuit.

At step 104, the determined patient metric can be compared to a threshold (TH), such as using the assessment circuit. If the determined patient metric exceeds the threshold, the MSP therapy mode can be implemented at step 105 (e.g., transitioning from the CRT mode to the MSP therapy mode), and process can return to step 102. In other examples, instead of implementing the MSP therapy mode, an indication to implement the MSP therapy mode can be provided, such as to a clinician or one or more other machines or processes via a notification or an alert, etc. If the determined patient metric does not exceed the threshold, the MSP therapy mode can remain off at step 106, and process can return to step 101. Separately from that described above with respect to FIG. 1, the present inventors have additionally recognized that certain physiologic information sensed from the patient in one or more time periods can be used to determine one or more CRT response metrics, and that such one or more determined CRT response metrics can be used to provide an alert or notification or otherwise control transition between different medical device modes, including, in certain examples, to: (1) control transition of a CRT mode to a non-CRT mode; (2) control transition of the CRT mode to an MSP therapy mode; or (3) to enable or disable the CRT mode. In certain examples, the alert itself is a notification that a determination has been made, taking in information from multiple sensors or sources and arriving at a determination.

In an example, the present inventors have recognized, among other things, that CRT responders and non-responders can be differentiated using differences in physiologic information of the patient, including one or more of heart sound information (e.g., first heart sound (S1) information, third heart sound (S3) information, etc.), ITTI information, activity level information, respiration rate information, RSBI information, or permutations or combinations thereof. In certain examples, a first medical device, such as one or more wearable or ambulatory medical devices, can be used to sense physiologic information from a patient to evaluate the patient as a likely responder to one or both of CRT or MSP therapy prior to implanting a second medical device (e.g., an implantable medical device) capable of or configured to provide one or both of CRT and MSP therapy, etc. The first medical device can sense or collect physiologic information of the patient from one or more sensors of the first or one or more other medical devices. The sensed or collected physiologic information of the patient can be analyzed prior to implanting the second medical device to determine a recommended type of second medical device (e.g., a device having a therapy mode coordinated to determined CRT response metrics), determination of recommended settings, such as therapy modes or parameters based on the analyzed physiologic information, etc.

As described above with respect to the Saba study, existing procedures to determine to implant a CRT device is patient condition (e.g., diagnosis of heart failure with myocardial dysfunction, etc.), resulting in 25% to 40% of CRT non-responders. Even with non-responders, there is monitoring value of the implanted CRT device, as the CRT device will detect physiologic information of the patient, determine patient status, and in certain examples, provide one or more other non-CRT functions (e.g., atrial or ventricular backup pacing, defibrillator functions, etc.). Although half of the CRT non-responders to respond to MSP therapy, that still results in 12% to 30% of patients undergoing an implant procedure for a CRT device that do not respond to CRT or MSP therapy. Additionally, even switching to MSP therapy mode results in additional use of CRT device resources that may otherwise be used to perform or extend the usable life of one or more other device functions. A determination has to be made as to whether or not, even in non-CRT responders, the switch to MSP is worth the resource use.

Using the first medical device to determine one or both of the CRT response metric or the MSP response metric prior to implant of the second medical device can aid selection of or provide one or more alerts or notifications indicating a recommended second medical device, in certain examples reducing otherwise unnecessary lead placement, streamlining implant procedures, or even omitting an implant procedure for the second medical device entirely.

Figure 2:
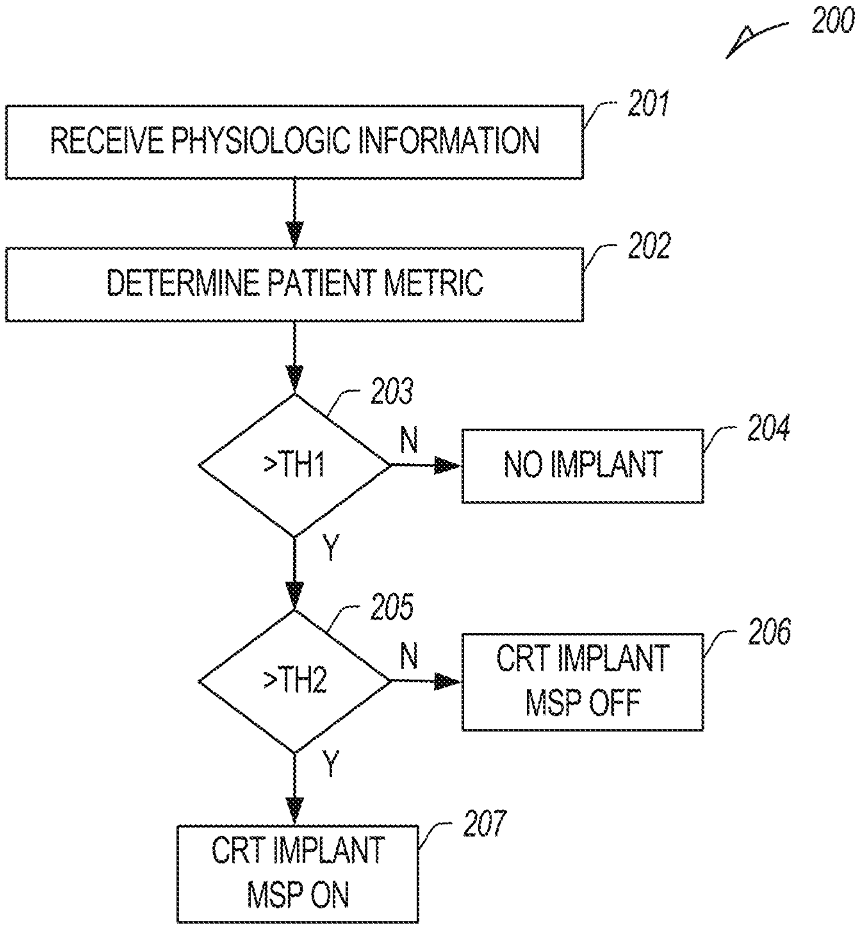
FIG. 2 illustrates an example process to determine one or more patient metrics prior to final selection or implant of the second medical device.

FIG. 2 illustrates an example process 200 to determine one or more patient metrics prior to final selection or implant of the second medical device. In certain examples, the one or more determined patient metrics can be used to select or determine the specific device for implant, a specific mode or therapy to be applied by the specific device, or even omit the implant entirely.

At step 201, physiologic information of a patient can be received from one or more sensors over a first time period using a first medical device, such as a wearable medical device (e.g., a patch-based medical device configured to be worn for an evaluation period, etc.), in certain examples using a signal receiver circuit. In certain examples, the one or more sensors can include sensors of the first medical device. In other examples, the first medical device can receive information from one or more sensors external to the first medical device. The received physiologic information can include one or more of heart sound information (e.g., S1, S3, etc.), ITTI information, activity level information, respiration rate information, RSBI information, or permutations or combinations thereof.

At step 202, a patient metric, such as one or more CRT or MSP response metrics, applicable with respect to a second medical device can be determined based on the received physiologic information, such as described herein, in certain examples using an assessment circuit. The one or more determined patient metrics can be compared to one or more thresholds, in certain examples as combinations of combined metrics or physiologic information to a threshold, as comparisons of separate metrics to specific thresholds, or combinations or permutations thereof. The one or more determined patient metrics can be used to determine whether a specific second medical device should be implanted in the patient, and if so, which mode should be implemented in the second medical device.

At step 203, the determined patient metric can be compared to a first threshold (TH1), such as using the assessment circuit. If the determined patient metric does not exceed the first threshold, the second medical device associated with the determined patient metric is not recommended (e.g., via an alert, a notification, etc.) at step 204. If the determined patient metric does exceed the first threshold, the second medical device (e.g., a device having or capable of providing a CRT mode, etc.) associated with the determined patient metric is recommended (e.g., via an alert, a notification, etc.), and process can proceed to step 205 to additionally determine if a specific mode (e.g., an MSP therapy mode) should be implemented on the second medical device.

At step 205, the determined patient metric can be compared to a second threshold (TH2), such as using the assessment circuit. If the determined patient metric does not exceed the second threshold, the second medical device associated with the determined patient metric (e.g., having or capable of providing a CRT mode, etc.) is recommended (e.g., via an alert, a notification, etc.) at step 206. If the determined patient metric does exceed the second threshold, the second medical device associated with the determined patient metric (e.g., having or capable of providing a CRT mode, etc.) is recommended, additionally with the specific mode (e.g., the MSP therapy mode) activated at step 207.

In certain examples, the one or more recommendations can be provided, once determined, to one or more other machines or processes, or one or more alerts can be provided to a clinician or user indicating that a recommendation (resulting from processing different data from different sensors or sources) has been determined, including an indication of the resulting recommendation.

For example, if the CRT response metric indicates a likely responder, the second medical device can be determined or selected as a device capable of CRT or having a CRT mode and an indication can be determined to implant the second medical device with the CRT mode on, in certain examples, with initial suggested settings determined using information from the first medical device. If the CRT response metric indicates a likely non-responder (e.g., a CRT response metric below a threshold) and the MSP response metric indicates a likely responder, the second medical device can be determined or selected as a device capable of MSP therapy or having an MSP therapy mode and an indication can be provided to implant the second medical device with the MSP therapy mode on, in certain examples, with initial suggested or recommended settings determined using information from the first medical device.

In an example, instead of an example patch or wearable device as the first medical device, in other examples, the first medical device can include the second medical device, only partially implanted, either in the pocket (e.g., implanted subcutaneously at a thorax of the patient, etc.) without the pocket being closed for the first time period of information collection, leaving the position open for different lead placement, etc. Alternatively, the second medical device can be implanted and used for the first time period before making the decision to implement CRT or MSP therapy in the patient using the second medical device, such that the second medical device acts as a data collection and analysis device prior to providing one or more therapies or implementing CRT or MSP therapy, etc.

To determine the one or more patient metrics, different physiologic information was analyzed over the first time period, or one or more other time periods (e.g., longer or shorter than the first time period). For example, heart sound information (e.g., S3/S1, etc.) and RSBI information were analyzed over a first period (e.g., 60 days post implant of the second medical device, etc.). Additionally, ITTI information and RSBI information were analyzed over a second period (e.g., 150 days post implant, including the first time period, etc.). Equation (1) above can be used to determine if a patient is likely to respond to the MSP therapy mode using one or both of ITTI information and RSBI information. In an example, the present inventors have recognized that heart sound information, and in certain examples, particularly S3/S1, is particularly well correlated to determining if a patient is likely to respond to a CRT mode (or CRT mode or MSP therapy mode), in contrast to being a non-responder (e.g., there is a difference in heart sound information between responders and non-responders). The present inventors have further recognized that RSBI information is similarly well correlated. In an example, the CRT response metric can be determined using one or both of heart sound information, such as S3/S1, etc., and RSBI information, in certain examples, further in combination with one or more other parameters. An example, equation (2), is provided below.

$$p(\mathrm{CRT}_{response}) \propto (\alpha \times (S3/S1) + (\beta \times \mathrm{RSBI}) \quad (2)$$

In equation (2), $p(\mathrm{CRT}_{response})$ is a patient metric (e.g., a CRT response metric), S3 is a third heart sound parameter (e.g., an amplitude or energy of the third heart sound, etc.), S1 is a first heart sound parameter (e.g., an amplitude or energy of the first heart sound, etc.), RSBI is a measure of patient respiration rate (RR) or frequency to a measure of tidal volume (e.g., RR/TV, etc.), and $\alpha$ and $\beta$ are variables. In other examples, the patient metric can be determined using a combination of this or other heart sound information (e.g., other than S3/S1, etc.), using only one of heart sound or RSBI information, using information over different time periods (e.g., 60 day periods, 150 day periods, etc.), or as different of one or more of such physiologic parameters in combination with one or more other physiologic parameters.

For example, a relatively high S3/S1 can indicate that the patient is likely to be a responder to CRT or MSP therapy. However, a relatively low S3/S1 can be combined with other information, such as one or more parameter from equation (1) above, to determine whether the patient is likely to be a responder to MSP therapy (and not CRT). Relatively high and low can be proportionate to the individual measures or determined by comparing data from responders and non-responders. In certain examples, the individual parameters can include differences, such as indicative of changes or variance in daily values over a period of time, etc.

Figure 3A:
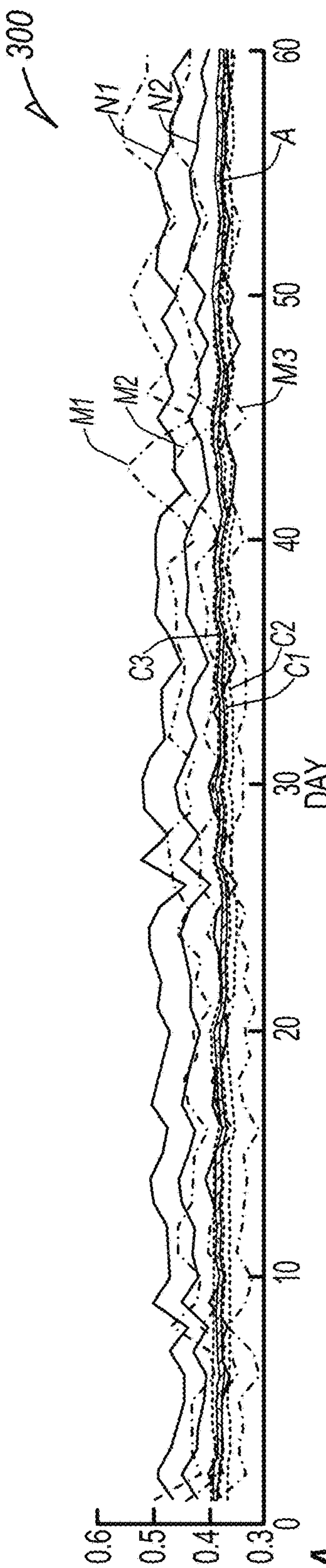
FIGS. 3A-C illustrate example heart sound information over a first time period for patients after implant of a CRT device.
Figure 3B:
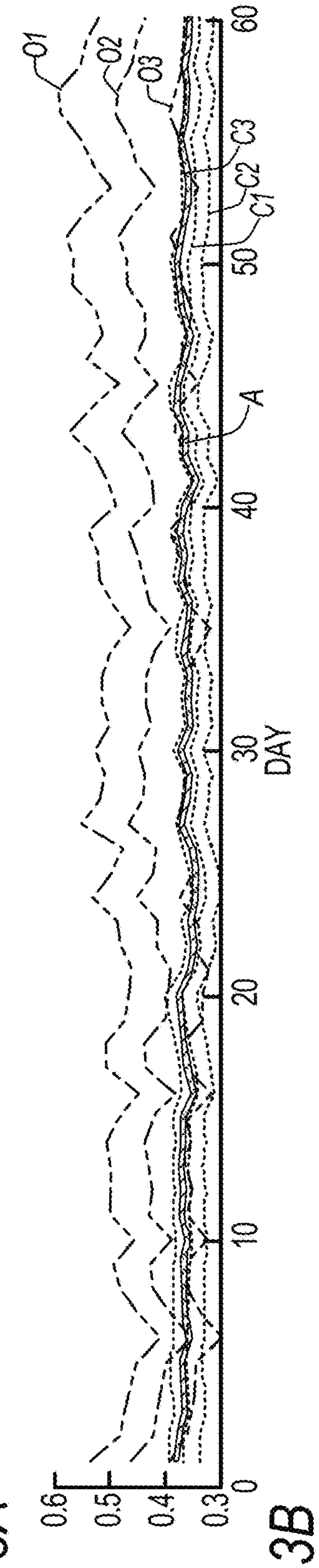
Figure 3C:
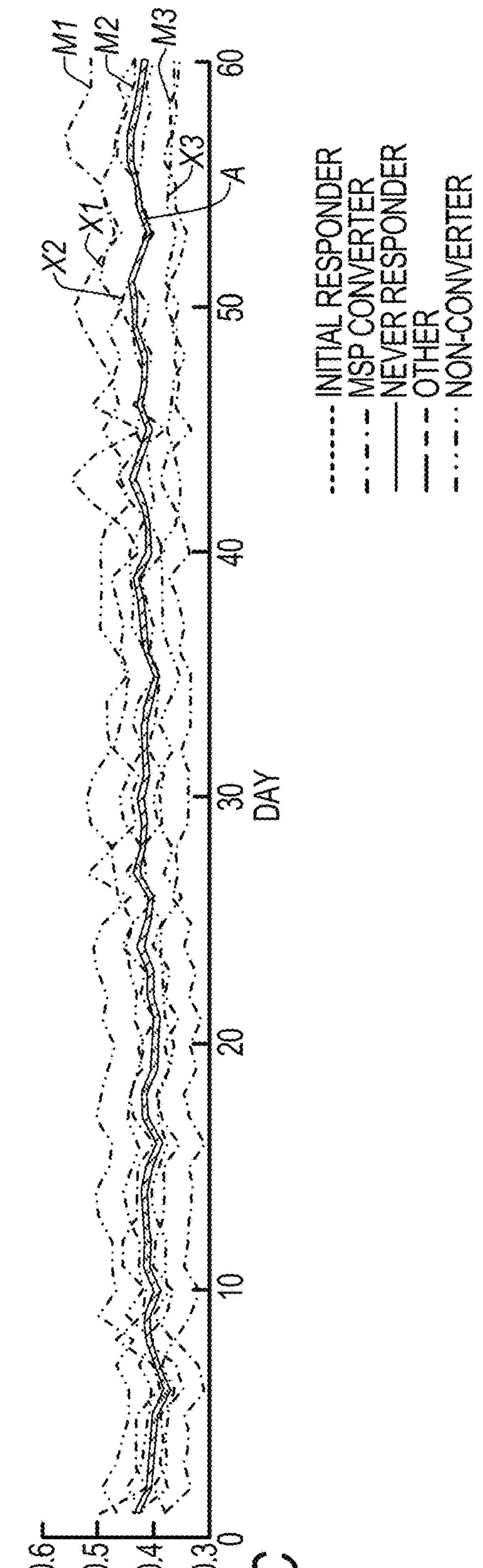

FIGS. 3A-C illustrate example heart sound information 300 (e.g., S3/S1) over a first time period (e.g., 60 days) for patients after implant of a CRT device. FIG. 3A illustrates example heart sound information of initial responders to CRT (marked "C"), subsequent responders to MSP therapy (marked "M"), and non-responders to both CRT and MSP therapy (marked "N"). FIG. 3B illustrates example heart sound information of initial responders (marked "C") and others (marked "O") (e.g., including subsequent responders to MSP therapy and non-responders, etc.). FIG. 3C illustrates example heart sound information of subsequent responders to MSP therapy (marked "M") and subsequent non-responders to MSP therapy (marked "X"). Each illustrated example also includes an average representation for the respective information illustrated as a wider, filled line (marked "A").

In certain examples, as illustrated above, heart sound information can be particularly well suited to distinguishing initial responders to CRT from non-responders or to distinguishing initial responders to CRT from other patients (e.g., subsequent responders to MSP therapy or non-responders to both CRT and MSP therapy, etc.).

Figures 4A, 4B, 4C:
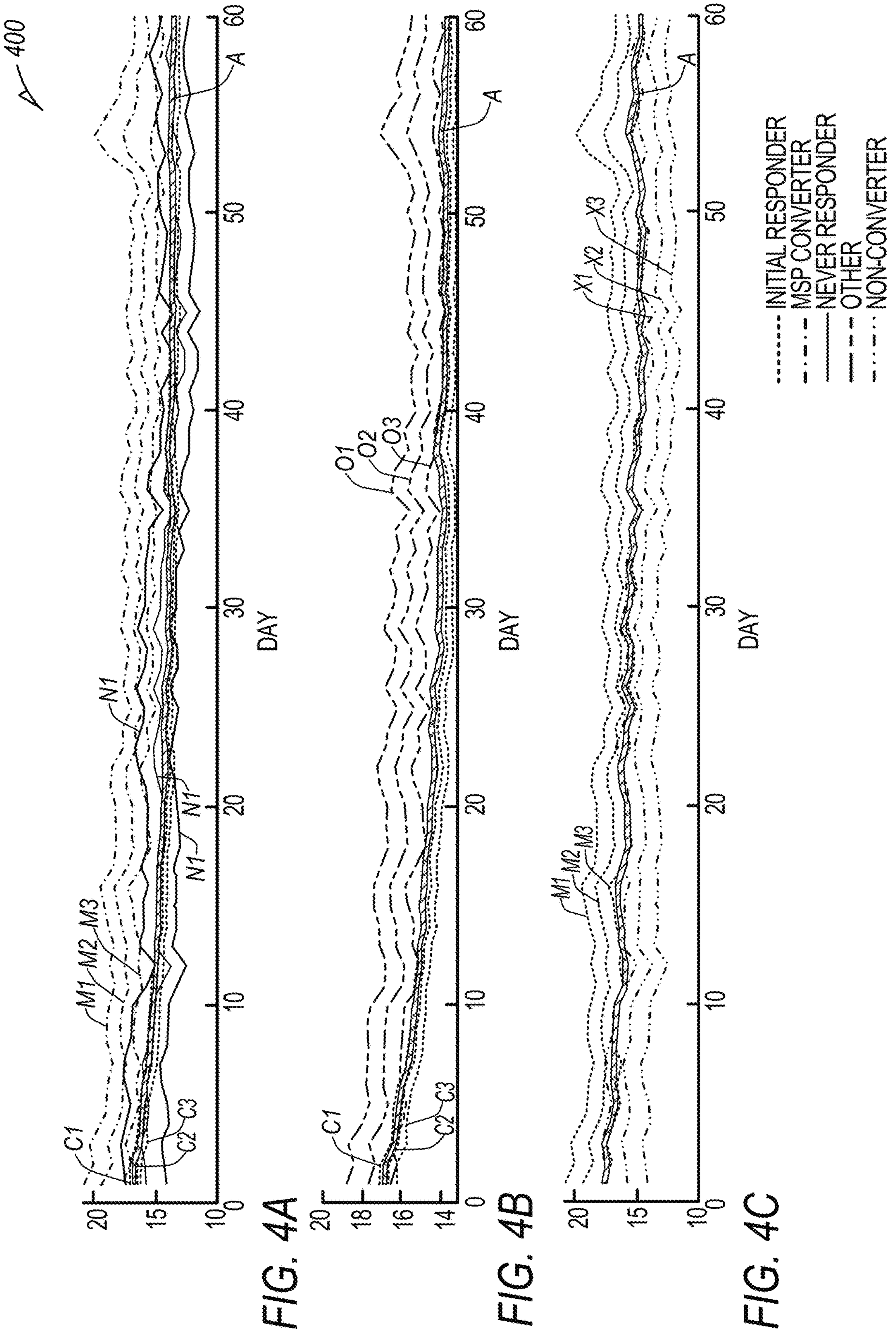
FIGS. 4A-C illustrate example RSBI information over a first time period for patients after implant of a CRT device.

FIGS. 4A-C illustrate example RSBI information 400 over a first time period (e.g., 60 days) for patients after implant of a CRT device. FIG. 4A illustrates example RSBI information of initial responders to CRT (marked "C"), subsequent responders to MSP therapy (marked "M"), and non-responders to both CRT and MSP therapy (marked "N"). FIG. 4B illustrates example RSBI information of initial responders (marked "C") and others (marked "O") (e.g., including subsequent responders to MSP therapy and non-responders, etc.). FIG. 4C illustrates example RSBI information of subsequent responders to MSP therapy (marked "M") and subsequent non-responders to MSP therapy (marked "X"). Each illustrated example also includes an average representation for the respective information illustrated as a wider, filled line (marked "A").

In certain examples, as illustrated above, RSBI information can be particularly well suited to distinguishing initial responders to CRT from other patients (e.g., subsequent responders to MSP or non-responders to both CRT and MSP therapy, etc.), to distinguishing between subsequent responders to MSP from other patients (e.g., initial responders to CRT or non-responders to both CRT and MSP therapy, etc.), or to distinguishing subsequent responders to MSP therapy from subsequent non-responders to MSP therapy.

In other examples, one or more other patient metrics can be determined using sensed or received physiologic information of the patient, or frequently using combinations of sensed or received physiologic information of the patient. The present inventors considered a variety of different physiologic information for determination of patient response metrics, including heart sound information (particularly S1 and S3 information), ITTI information, respiration rate information, RSBI information, night heart rate information, activity information, and a multi-sensor HeartLogic index.

The HeartLogic index is a composite heart failure risk indication determined using a combination of different physiologic information, including heart sound information (including S1 and S3), respiration rate and volume information, ITTI information, heart rate information (e.g., particularly night heart rate determined between midnight and 6 am with respect to the patient), and daily patient activity information (e.g., daily hours above an activity threshold).

From a randomly selected 60% development set of patients (183 CRT responders and 40 CRT non-responders), the following statistical measures were calculated for each parameter based on the first 150-day epoch after implant of a cardiac rhythm therapy device: overall mean ($\mu$150), mean over first ($\mu$F30) or last 30 days ($\mu$L30) of the epoch, and standard deviation ($\sigma$150). To evaluate the effect of each measure on response or non-response, odds ratios were calculated and tested for significance. Based on the initial univariate analysis, measures with a $p\text{-value}<0.15$ were subsequently included in a multivariate logistic regression model with backwards elimination to achieve $p<0.05$ for the remaining variables.

Increases in 150-day variability ($\sigma$150) of S3, S3/S1 ratio, RSBI, respiration rate, and HeartLogic index were significantly associated with reduced odds of a positive response to CRT in a univariate model. Similarly, increases in RSBI, respiration rate, and HeartLogic index averages were significantly associated with reduced odds of a positive response to CRT. Multiple device-based physiologic parameters significantly differed between responders and non-responders to CRT. Respiration rate variability and daily activity remained significant in multivariate analysis.

Accordingly, the present inventors have recognized, unexpectedly, that respiration variability information (e.g., respiration rate variability (e.g., 1 BPM change), etc.) and daily activity information (e.g., the amount of time the patient is active above a threshold, the number of hours having patient activity above a threshold, etc.) are strong indicators of CRT response or non-response. In certain examples, a patient metric can be determined using one or more of the respiration variability information or the daily activity information to identify patients that may respond to one or both of CRT or MSP therapy, to identify patients that may benefit from switching to MSP therapy from CRT, and in certain examples, to distinguish MSP therapy responders and non-responders once providing MSP therapy. An assessment circuit can be configured to provide one or more alerts, make one or more recommendations, or provide one or more control signals to control generation or delivery of one or more stimulation signals or implementation of one or more different stimulation modes.

Figure 5:
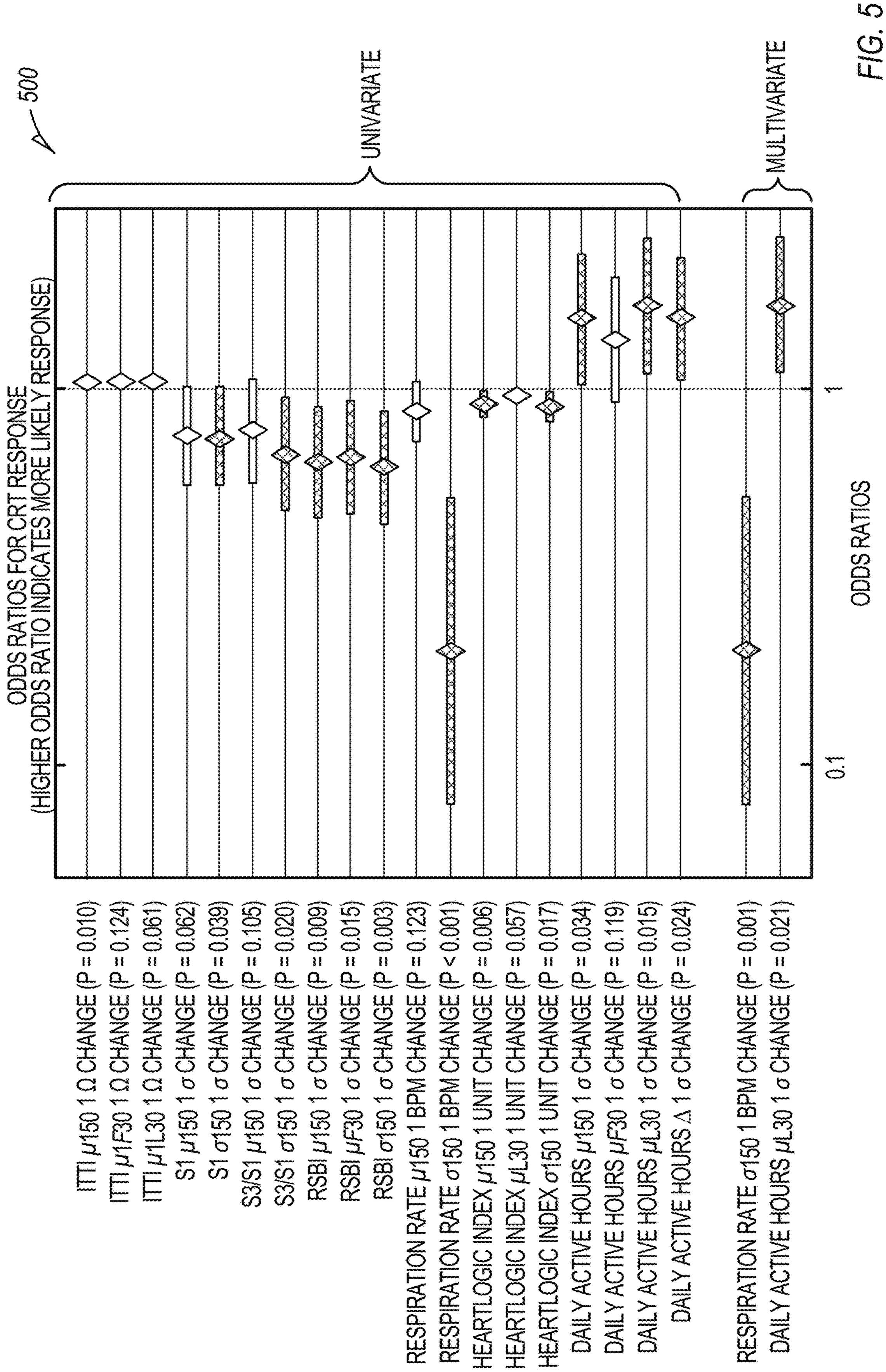
FIG. 5 illustrates determined odds ratios for physiologic information associated with response to CRT.

FIG. 5 illustrates determined odds ratios 500 for physiologic information associated with response to CRT with 95% confidence intervals per 1 unit or standard deviation change. An odds ratio of 1 does not affect outcome. In contrast, odds ratios further away from 1 indicate greater effect on outcome, with an odds ratio greater than 1 associated with higher odds of outcome and an odds ratio less than 1 associated with lower odds of outcome. The different odds are marked on a line centered with a diamond, with patterned odds indicating a significant value in contrast to unpatterned odds. A multivariable model started with the measures having p-value<0.15 in the univariable analysis and was reduced using backwards elimination, identifying the most significant indications. Although respiration variability and daily activity were most significant, other physiologic information still held significant value, including heart sound information (e.g., S3, S3/S1, etc.), RSBI information, and in certain examples, the HeartLogic index.

In an example, a patient metric can be determined using patient physiologic information, such as one or more of respiration variability information or daily activity information, or in certain examples, heart sound information, RSBI information, or combinations or permutations thereof. In certain examples, the determined patient metric can indicate a need for CRT, MSP therapy, or combinations thereof, or that the patient is a likely responder or non-responder to CRT or MSP therapy. In other examples, the determined patient metric can be used to control transition between therapy modes, such as to transition into, between, or out of one or more of a CRT mode and a MSP therapy mode, etc.

The following features were found to correlate to CRT response, identified as most significant indications, as discussed above: HeartLogic index (e.g., HeartLogic index rough mode, HeartLogic index days over population mean); ITTI (e.g., ITTI max real FFT (Fast Fourier Transform); respiration rate (e.g., RR standard deviation); activity (e.g., change in activity from first 30 days to last 30 days of evaluation period); etc.

The following features were found to correlate to subsequent responders to MSP therapy, identified as most significant indications, as discussed above: ITTI (e.g., ITTI rough mode, ITTI days over population mean); RSBI (e.g., RSBI power spectral density (PSD) peak width, RSBI days over population mean); etc. In other examples, other significant features can include: RR (e.g., RR FFT image max, RR mean, RR mean last 30 (last 30 days of evaluation period)); S3 (e.g., S3 late mean); RSBI (e.g., RSBI mean 30 days before switch to MSP therapy from CRT, RSBI mean last 30); ITTI (e.g., ITTI standard deviation); HR (e.g., HR delta), etc.

Respiration and intrathoracic impedance drive predictions of both CRT and subsequent MSP response. HeartLogic and activity level are also useful in predicting initial CRT response. Determinations of MSP response metrics were found to be more impactful when using RSBI in contrast to RR. Accordingly, with respect to MSP response, tidal volume (TV) can be a driving factor in determinations of MSP response metrics.

Figure 6:
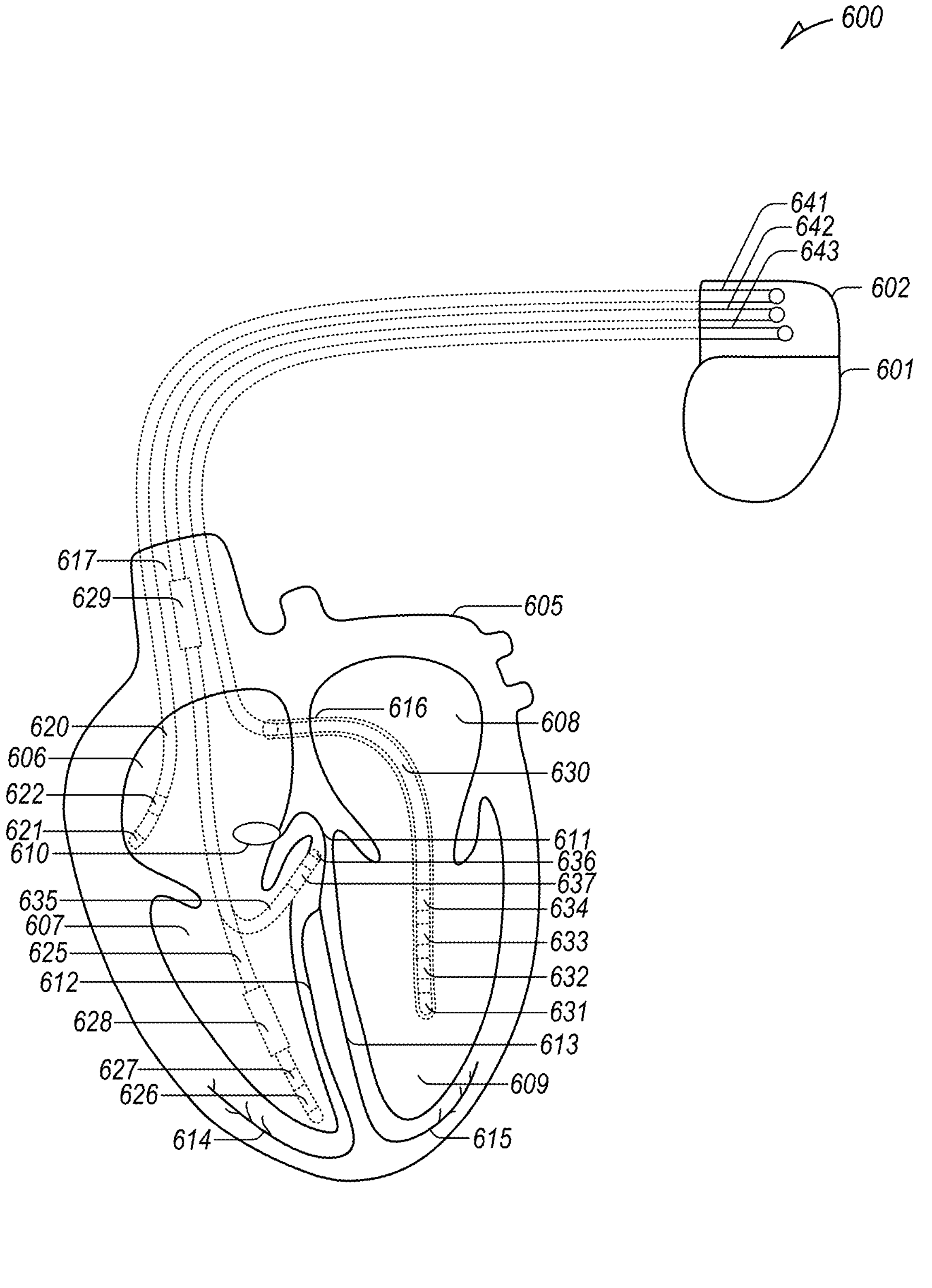
FIG. 6 illustrates an example implantable medical device (IMD) electrically coupled to a heart.

FIG. 6 illustrates an implantable medical device (IMD) 600 electrically coupled to a heart 605, such as through one or more leads coupled to the IMD 600 through one or more lead ports, such as first, second, or third lead ports 641, 642, 643 in a header 602 of the IMD 600. In an example, the IMD 600 can include an antenna, such as in the header 602, configured to enable communication with an external system and one or more electronic circuits (e.g., an assessment circuit, etc.) in a hermetically sealed housing (CAN) 601.

The IMD 600 may include an implantable medical device (IMD), such as an implantable cardiac monitor (ICM), pacemaker, defibrillator, cardiac resynchronizer, or other subcutaneous IMD or cardiac rhythm management (CRM) device configured to be implanted in a chest of a subject, having one or more leads to position one or more electrodes or other sensors at various locations in or near the heart 605, such as in one or more of the atria or ventricles. Separate from, or in addition to, the one or more electrodes or other sensors of the leads, the IMD 600 can include one or more electrodes or other sensors (e.g., a pressure sensor, an accelerometer, a gyroscope, a microphone, etc.) powered by a power source in the IMD 600. The one or more electrodes or other sensors of the leads, the IMD 600, or a combination thereof, can be configured detect physiologic information from, or provide one or more therapies or stimulation to, the patient.

The IMD 600 can include one or more electronic circuits configured to sense one or more physiologic signals, such as an electrogram or a signal representing mechanical function of the heart 605. In certain examples, the CAN 601 may function as an electrode such as for sensing or pulse delivery. For example, an electrode from one or more of the leads may be used together with the CAN 601 such as for unipolar sensing of an electrogram or for delivering one or more pacing pulses. A defibrillation electrode (e.g., the first defibrillation coil electrode 628, the second defibrillation coil electrode 629, etc.) may be used together with the CAN 601 to deliver one or more cardioversion/defibrillation pulses.

In an example, the IMD 600 can sense impedance such as between electrodes located on one or more of the leads or the CAN 601. The IMD 600 can be configured to inject current between a pair of electrodes, sense the resultant voltage between the same or different pair of electrodes, and determine impedance, such as using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing, etc. In an example, the IMD 600 can be configured to inject current between an electrode on one or more of the first, second, third, or fourth leads 620, 625, 630, 635 and the CAN 601, and to sense the resultant voltage between the same or different electrodes and the CAN 601.

The example lead configurations in FIG. 6 include first, second, and third leads 620, 625, 630 in traditional lead placements in the right atrium (RA) 606, right ventricle (RV)

607, and in a coronary vein 616 (e.g., the coronary sinus) over the left atrium (LA) 608 and left ventricle (LV) 609, respectively, and a fourth lead 635 positioned in the RV 607 near the His bundle 611, between the AV node 610 and the right and left bundle branches 612, 613 and Purkinje fibers 614, 615. Each lead can be configured to position one or more electrodes or other sensors at various locations in or near the heart 605 to detect physiologic information or provide one or more therapies or stimulation.

The first lead 620, positioned in the RA 606, includes a first tip electrode 621 located at or near the distal end of the first lead 620 and a first ring electrode 622 located near the first tip electrode 621. The second lead 625 (dashed), positioned in the RV 607, includes a second tip electrode 626 located at or near the distal end of the second lead 625 and a second ring electrode 627 located near the second tip electrode 626. The third lead 630, positioned in the coronary vein 616 over the LV 609, includes a third tip electrode 631 located at or near the distal end of the third lead 630, a third ring electrode 632 located near the third tip electrode 631, and two additional electrodes 633, 634. The fourth lead 635, positioned in the RV 607 near the His bundle 611, includes a fourth tip electrode 636 located at or near the distal end of the fourth lead 635 and a fourth ring electrode 637 located near the fourth tip electrode 636. The tip and ring electrodes can include pacing/sensing electrodes configured to sense electrical activity or provide pacing stimulation.

In addition to tip and ring electrodes, one or more leads can include one or more defibrillation coil electrodes configured to sense electrical activity or provide cardioversion or defibrillation shock energy. For example, the second lead 625 includes a first defibrillation coil electrode 628 located near the distal end of the second lead 625 in the RV 607 and a second defibrillation coil electrode 629 located a distance from the distal end of the second lead 625, such as for placement in or near the superior vena cava (SVC) 617.

Different CRM devices include different number of leads and lead placements. For examples, some CRM devices are single-lead devices having one lead (e.g., RV only, RA only, etc.). Other CRM devices are multiple-lead devices having two or more leads (e.g., RA and RV; RV and LV; RA, RV, and LV; etc.). CRM devices adapted for His bundle pacing often use lead ports designated for LV or RV leads to deliver stimulation to the His bundle 611.

Figure 7:
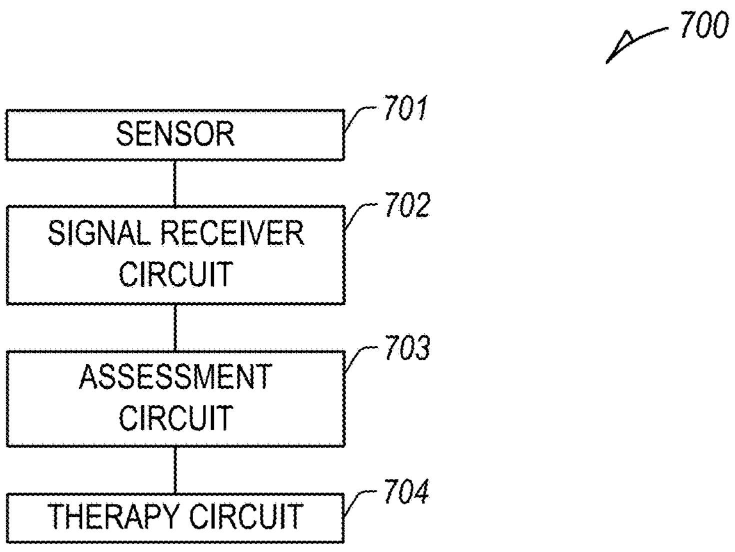
FIG. 7 illustrates an example medical device system.

FIG. 7 illustrates an example system 700 (e.g., a medical device system). In an example, one or more aspects of the example system 700 can be a component of, or communicatively coupled to, a medical device, such as an implantable medical device (IMD), an insertable cardiac monitor, an ambulatory medical device (AMD), etc. The system 700 can be configured to monitor, detect, or treat various physiologic conditions of the body, such as cardiac conditions associated with a reduced ability of a heart to sufficiently deliver blood to a body, including heart failure, arrhythmias, dyssynchrony, etc., or one or more other physiologic conditions and, in certain examples, can be configured to provide electrical stimulation or one or more other therapies or treatments to the patient.

The system 700 can include a single medical device or a plurality of medical devices implanted in a patient's body or otherwise positioned on or about the patient to monitor patient physiologic information of the patient using one or more sensors, such as a sensor 701. In an example, the sensor 701 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., an intrathoracic impedance sensor, a transthoracic impedance sensor, a thoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a temperature sensor; a skin elasticity sensor, or one or more other sensors configured to receive physiologic information of the patient.

The example system 700 can include a signal receiver circuit 702 and an assessment circuit 703. The signal receiver circuit 702 can be configured to receive physiologic information of a patient (or group of patients) from the sensor 701. The assessment circuit 703 can be configured to receive information from the signal receiver circuit 702, and to determine one or more parameters (e.g., physiologic parameters, stratifiers, etc.) or existing or changed patient conditions (e.g., indications of patient dehydration, respiratory condition, cardiac condition (e.g., heart failure, arrhythmia), sleep disordered breathing, etc.) using the received physiologic information, such as described herein. The physiologic information can include, among other things, cardiac electrical information, impedance information, respiration information, heart sound information, activity information, posture information, temperature information, or one or more other types of physiologic information.

In certain examples, the assessment circuit 703 can aggregate information from multiple sensors or devices, detect various events using information from each sensor or device separately or in combination, update a detection status for one or more patients based on the information, and transmit a message or an alert to one or more remote devices that a detection for the one or more patients has been made or that information has been stored or transmitted, such that one or more additional processes or systems can use the stored or transmitted detection or information for one or more other review or processes.

In certain examples, such as to detect an improved or worsening patient condition, some initial assessment is often required to establish a baseline level or condition from one or more sensors or physiologic information. Subsequent detection of a deviation from the baseline level or condition can be used to determine the improved or worsening patient condition. However, in other examples, the amount of variation or change (e.g., relative or absolute change) in physiologic information over different time periods can used to determine a risk of an adverse medical event, or to predict or stratify the risk of the patient experiencing an adverse medical event (e.g., a heart failure event) in a period following the detected change, in combination with or separate from any baseline level or condition.

Changes in different physiologic information can be aggregated and weighted based on one or more patient-specific stratifiers and, in certain examples, compared to one or more thresholds, for example, having a clinical sensitivity and specificity across a target population with respect to a specific condition (e.g., heart failure), etc., and one or more specific time periods, such as daily values, short term averages (e.g., daily values aggregated over a number of days), long term averages (e.g., daily values aggregated over a number of short term periods or a greater number of days (sometimes different (e.g., non-overlapping) days than used for the short term average)), etc.

The assessment circuit 703 can be configured to provide an output to a user, such as to a display or one or more other user interface, the output including a score, a trend, an alert, or other indication. In other examples, the assessment circuit 703 can be configured to provide an output to another circuit, machine, or process, such as a therapy circuit 704 (e.g., a cardiac resynchronization therapy (CRT) circuit, a chemical therapy circuit, a stimulation circuit, etc.), etc., to control, adjust, or cease a therapy of a medical device, a drug delivery system, etc., or otherwise alter one or more processes or functions of one or more other aspects of a medical device system, such as one or more CRT parameters, drug delivery, dosage determinations or recommendations, etc. In an example, the therapy circuit 704 can include one or more of a stimulation control circuit, a cardiac stimulation circuit, a neural stimulation circuit, a dosage determination or control circuit, etc. In other examples, the therapy circuit 704 can be controlled by the assessment circuit 703, or one or more other circuits, etc.

A technological problem exists in medical devices and medical device systems that in low-power monitoring modes, ambulatory medical devices powered by one or more rechargeable or non-rechargeable batteries (e.g., including IMDs) have to make certain tradeoffs between battery life, or in the instance of implantable medical devices with non-rechargeable batteries, between device replacement periods often including surgical procedures, and sampling resolution, sampling periods, of processing, storage, and transmission of sensed physiologic information, or features or mode selection of or within the medical devices. Medical devices can include higher-power modes and lower-power modes. Physiologic information, such as indicative of a potential adverse physiologic event, can be used to transition from a low-power mode to a high-power mode. In certain examples, the low-power mode can include a low resource mode, characterized as requiring less power, processing time, memory, or communication time or bandwidth (e.g., transferring less data, etc.) than a corresponding high-power mode. The high-power mode can include a relatively higher resource mode, characterized as requiring more power, processing time, memory, or communication time or bandwidth than the corresponding low-power mode. However, by the time physiologic information detected in the low-power mode indicates a possible event, valuable information has been lost, unable to be recorded in the high-power mode.

The inverse is also true, in that false or inaccurate determinations that trigger a high-power mode unnecessarily unduly limit the usable life of certain ambulatory medical devices. For numerous reasons, it is advantageous to accurately detect and determine physiologic events, and to avoid unnecessary transitions from the low-power mode to the high-power mode to improve use of medical device resources.

Figure 8:
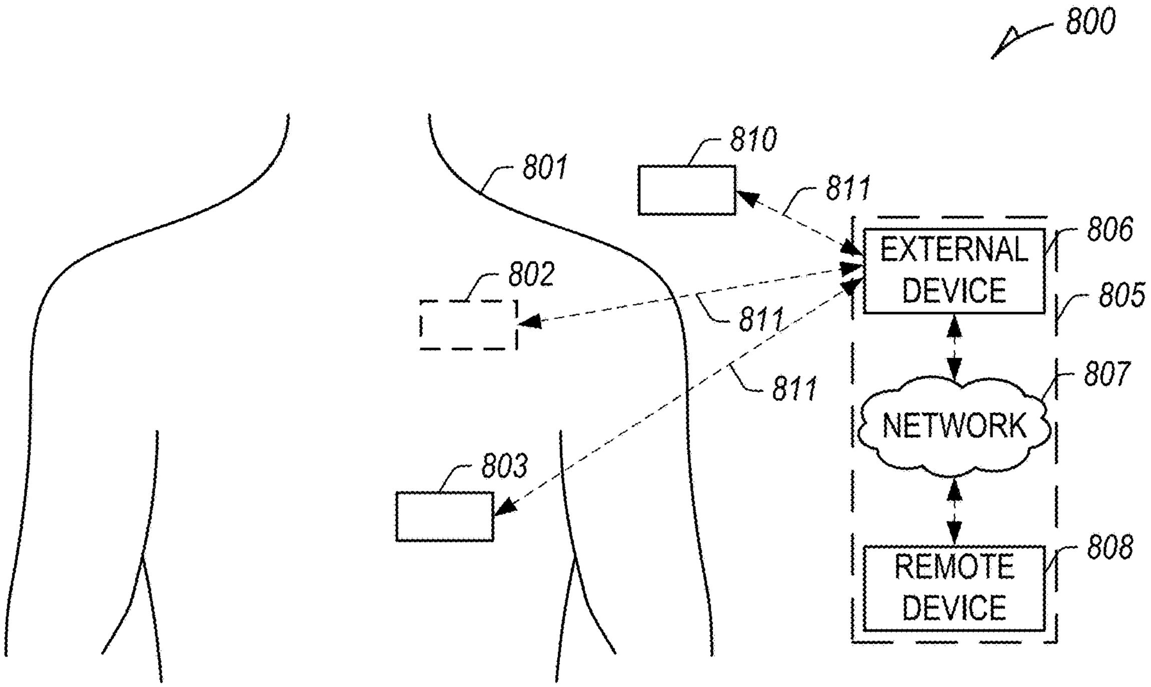
FIG. 8 illustrates an example patient management system.

FIG. 8 illustrates an example patient management system 800 and portions of an environment in which the patient management system 800 may operate. The patient management system 800 can perform a range of activities, including remote patient monitoring and diagnosis of a disease condition. Such activities can be performed proximal to a patient 801, such as in a patient home or office, through a centralized server, such as in a hospital, clinic, or physician office, or through a remote workstation, such as a secure wireless mobile computing device.

The patient management system 800 can include one or more medical devices, an external system 805, and a communication link 811 providing for communication between the one or more ambulatory medical devices and the external system 805. The one or more medical devices can include an ambulatory medical device (AMD), such as an implantable medical device (IMD) 802, a wearable medical device 803, or one or more other implantable, leadless, subcutaneous, external, wearable, or medical devices configured to monitor, sense, or detect information from, determine physiologic information about, or provide one or more therapies to treat various conditions of the patient 801, such as one or more cardiac or non-cardiac conditions (e.g., dehydration, sleep disordered breathing, etc.).

In an example, the implantable medical device 802 can include one or more cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 801. In another example, the implantable medical device 802 can include a monitor implanted, for example, subcutaneously in the chest of patient 801, the implantable medical device 802 including a housing containing circuitry and, in certain examples, one or more sensors, such as a temperature sensor, etc.

Cardiac rhythm management devices, such as insertable cardiac monitors, pacemakers, defibrillators, or cardiac resynchronizers, include implantable or subcutaneous devices having hermetically sealed housings configured to be implanted in a chest of a patient. The cardiac rhythm management device can include one or more leads to position one or more electrodes or other sensors at various locations in or near the heart, such as in one or more of the atria or ventricles of a heart, etc. Accordingly, cardiac rhythm management devices can include aspects located subcutaneously, though proximate the distal skin of the patient, as well as aspects, such as leads or electrodes, located near one or more organs of the patient. Separate from, or in addition to, the one or more electrodes or other sensors of the leads, the cardiac rhythm management device can include one or more electrodes or other sensors (e.g., a pressure sensor, an accelerometer, a gyroscope, a microphone, etc.) powered by a power source in the cardiac rhythm management device. The one or more electrodes or other sensors of the leads, the cardiac rhythm management device, or a combination thereof, can be configured detect physiologic information from the patient, or provide one or more therapies or stimulation to the patient.

Implantable devices can additionally or separately include leadless cardiac pacemakers (LCPs), small (e.g., smaller than traditional implantable cardiac rhythm management devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable cardiac rhythm management device complications (e.g., required incision and pocket, complications associated with lead placement, breakage, or migration, etc.). In certain examples, leadless cardiac pacemakers can have more limited power and processing capabilities than a traditional cardiac rhythm management device; however, multiple leadless cardiac pacemakers can be implanted in or about the heart to detect physiologic information from, or provide one or more therapies or stimulation to, one or more chambers of the heart. The multiple leadless cardiac pacemaker can communicate between themselves, or one or more other implanted or external devices.

The implantable medical device 802 can include an assessment circuit configured to detect or determine specific physiologic information of the patient 801, or to determine one or more conditions or provide information or an alert to a user, such as the patient 801 (e.g., a patient), a clinician, or one or more other caregivers or processes, such as described herein. The implantable medical device 802 can alternatively or additionally be configured as a therapeutic device configured to treat one or more medical conditions of the patient 801. The therapy can be delivered to the patient 801 via the lead system and associated electrodes or using one or more other delivery mechanisms. The therapy can include delivery of one or more drugs to the patient 801, such as using the implantable medical device 802 or one or more of the other ambulatory medical devices, etc. In some examples, therapy can include CRT for rectifying dyssynchrony and improving cardiac function in heart failure patients. In other examples, the implantable medical device 802 can include a drug delivery system, such as a drug infusion pump to deliver drugs to the patient for managing arrhythmias or complications from arrhythmias, hypertension, hypotension, or one or more other physiologic conditions. In other examples, the implantable medical device 802 can include one or more electrodes configured to stimulate the nervous system of the patient or to provide stimulation to the muscles of the patient airway, etc.

The wearable medical device 803 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

The external system 805 can include a dedicated hardware/software system, such as a programmer, a remote server-based patient management system, or alternatively a system defined predominantly by software running on a standard personal computer. The external system 805 can manage the patient 801 through the implantable medical device 802 or one or more other ambulatory medical devices connected to the external system 805 via a communication link 811. In other examples, the implantable medical device 802 can be connected to the wearable medical device 803, or the wearable medical device 803 can be connected to the external system 805, via the communication link 811. This can include, for example, programming the implantable medical device 802 to perform one or more of acquiring physiologic data, performing at least one self-diagnostic test (such as for a device operational status), analyzing the physiologic data, or optionally delivering or adjusting a therapy for the patient 801. Additionally, the external system 805 can send information to, or receive information from, the implantable medical device 802 or the wearable medical device 803 via the communication link 811. Examples of the information can include real-time or stored physiologic data from the patient 801, diagnostic data, such as detection of patient hydration status, hospitalizations, responses to therapies delivered to the patient 801, or device operational status of the implantable medical device 802 or the wearable medical device 803 (e.g., battery status, lead impedance, etc.). The communication link 811 can be an inductive telemetry link, a capacitive telemetry link, or a radio-frequency (RF) telemetry link, or wireless telemetry based on, for example, "strong" Bluetooth or IEEE 602.11 wireless fidelity "Wi-Fi" interfacing standards. Other configurations and combinations of patient data source interfacing are possible.

The external system 805 can include an external device 806 in proximity of the one or more ambulatory medical devices, and a remote device 808 in a location relatively distant from the one or more ambulatory medical devices, in communication with the external device 806 via a communication network 807. Examples of the external device 806 can include a medical device programmer. The remote device 808 can be configured to evaluate collected patient or patient information and provide alert notifications, among other possible functions. In an example, the remote device 808 can include a centralized server acting as a central hub for collected data storage and analysis from a number of different sources. Combinations of information from the multiple sources can be used to make determinations and update individual patient status or to adjust one or more alerts or determinations for one or more other patients. The server can be configured as a uni-, multi-, or distributed computing and processing system. The remote device 808 can receive data from multiple patients. The data can be collected by the one or more ambulatory medical devices, among other data acquisition sensors or devices associated with the patient 801. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 808 may additionally include one or more locally configured clients or remote clients securely connected over the communication network 807 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 808, including the server and the interconnected clients, may also execute a follow-up scheme by sending follow-up requests to the one or more ambulatory medical devices, or by sending a message or other communication to the patient 801 (e.g., the patient), clinician or authorized third party as a compliance notification.

The communication network 807 can provide wired or wireless interconnectivity. In an example, the communication network 807 can be based on the Transmission Control Protocol/Internet Protocol (TCP/IP) network communication specification, although other types or combinations of networking implementations are possible. Similarly, other network topologies and arrangements are possible.

One or more of the external device 806 or the remote device 808 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 806 or the remote device 808 can include a respective display unit for displaying the physiologic or functional signals, or alerts, alarms, emergency calls, or other forms of warnings to signal the detection of arrhythmias. In some examples, the external system 805 can include an external data processor configured to analyze the physiologic or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 805 can be implemented using hardware, software, firmware, or combinations thereof. Portions of the one or more ambulatory medical devices or the external system 805 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The therapy device 810 can be configured to send information to or receive information from one or more of the ambulatory medical devices or the external system 805 using the communication link 811. In an example, the one or more ambulatory medical devices, the external device 806, or the remote device 808 can be configured to control one or more parameters of the therapy device 810. The external system 805 can allow for programming the one or more ambulatory medical devices and can receives information about one or more signals acquired by the one or more ambulatory medical devices, such as can be received via a communication link 811. The external system 805 can include a local external implantable medical device programmer. The external system 805 can include a remote patient management system that can monitor patient status or adjust one or more therapies such as from a remote location.

Ambulatory medical devices can additionally include or be configured to receive mechanical acceleration information from one or more accelerometer sensors to determine and monitor patient acceleration information, such as cardiac vibration information associated with blood flow or movement in the heart or patient vasculature (e.g., heart sounds, cardiac wall motion, etc.), patient physical activity or position information (e.g., patient posture, activity, etc.), respiration information (e.g., respiration rate, phase, breathing sounds, etc.), etc.

Heart sounds are recurring mechanical signals associated with cardiac vibrations or accelerations from blood flow through the heart or other cardiac movements with each cardiac cycle or interval and can be separated and classified according to activity associated with such vibrations, accelerations, movements, pressure waves, or blood flow. Heart sounds include four major features: the first through the fourth heart sounds (S1 through S4, respectively). The first heart sound (S1) is the vibrational sound made by the heart during closure of the atrioventricular (AV) valves, the mitral valve and the tricuspid valve, and the opening of the aortic valve at the beginning of systole, or ventricular contraction. The second heart sound (S2) is the vibrational sound made by the heart during closure of the aortic and pulmonary valves at the beginning of diastole, or ventricular relaxation. The third and fourth heart sounds (S3, S4) are related to filling pressures of the left ventricle during diastole. An abrupt halt of early diastolic filling can cause the third heart sound (S3). Vibrations due to atrial kick can cause the fourth heart sound (S4). Valve closures and blood movement and pressure changes in the heart can cause accelerations, vibrations, or movement of the cardiac walls that can be detected using an accelerometer or a microphone, providing an output referred to herein as cardiac acceleration information.

In an example, the heart sound parameter can include an ensemble average of a particular heart sound over a heart sound waveform, such as that disclosed in the commonly assigned Siejko et al. U.S. Pat. No. 7,115,096 entitled "THIRD HEART SOUND ACTIVITY INDEX FOR HEART FAILURE MONITORING," or in the commonly assigned Patangay et al. U.S. Pat. No. 7,853,327 entitled "HEART SOUND TRACKING SYSTEM AND METHOD," each of which are hereby incorporated by reference in their entireties, including their disclosures of ensemble averaging an acoustic signal and determining a particular heart sound of a heart sound waveform.

In certain examples, event storage can be triggered, such as received physiologic information or in response to one or more detected events or determined parameters meeting or exceeding a threshold (e.g., a static threshold, a dynamic threshold, or one or more other thresholds based on patient or population information, etc.). Information sensed or recorded in the high-power mode can be transitioned from short-term storage, such as in a loop recorder, to long-term or non-volatile memory, or in certain examples, prepared for communication to an external device separate from the medical device. In an example, cardiac electrical or cardiac mechanical information leading up to and in certain examples including the detected atrial fibrillation event can be stored, such as to increase the specificity of detection. In an example, multiple loop recorder windows (e.g., 2-minute windows) can be stored sequentially. In systems without early detection, to record this information, a loop recorder with a longer time period would be required at substantial additional cost (e.g., power, processing resources, component cost, amount of memory, etc.). Storing multiple windows using this early detection leading up to a single event can provide full event assessment with power and cost savings, in contrast to the longer loop recorder windows. In addition, the early detection can trigger additional parameter computation or storage, at different resolution or sampling frequency, without unduly taxing finite system resources.

In certain examples, one or more alerts can be provided, such as to the patient, to a clinician, or to one or more other caregivers (e.g., using a patient smart watch, a cellular or smart phone, a computer, etc.), such as in response to the transition to the high-power mode, in response to the detected event or condition, or after updating or transmitting information from a first device to a remote device. In other examples, the medical device itself can provide an audible or tactile alert to warn the patient of the detected condition. For example, the patient can be alerted in response to a detected condition so they can engage in corrective action, such as sitting down, etc.

In certain examples, a therapy can be provided in response to the detected condition. For example, a pacing therapy can be provided, enabled, or adjusted, such as to disrupt or reduce the impact of the detected atrial fibrillation event. In other examples, delivery of one or more drugs (e.g., a vasoconstrictor, pressor drugs, etc.) can be triggered, provided, or adjusted, such as using a drug pump, in response to the detected condition, alone or in combination with a pacing therapy, such as that described above, such as to increase arterial pressure, maintain cardiac output, and to disrupt or reduce the impact of the detected atrial fibrillation event.

Figure 9:
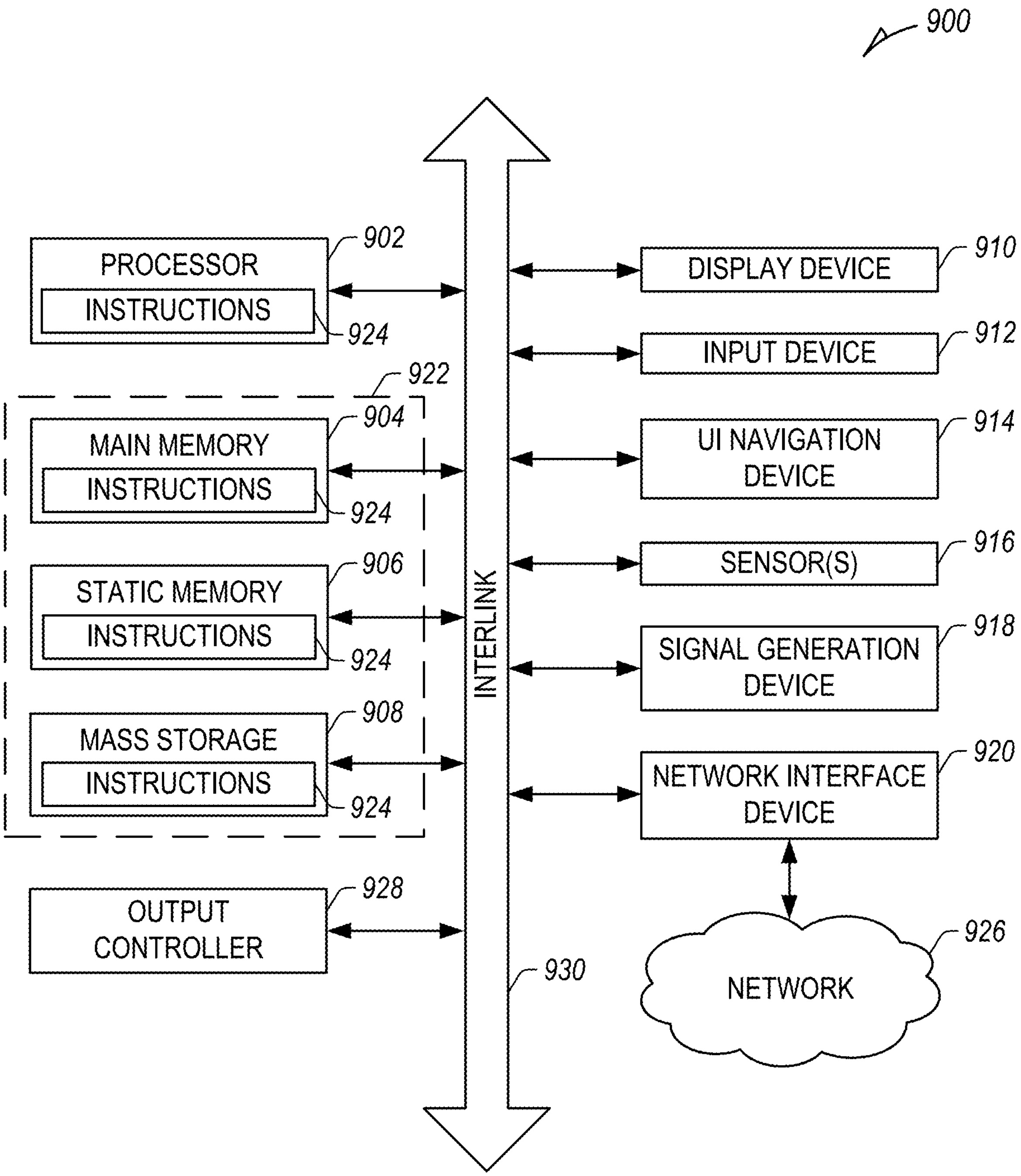
FIG. 9 illustrates a block diagram of an example machine upon which any one or more of the techniques discussed herein may perform.

FIG. 9 illustrates a block diagram of an example machine 900 upon which any one or more of the techniques (e.g., methodologies) discussed herein may perform. Portions of this description may apply to the computing framework of one or more of the medical devices described herein, such as the implantable medical device, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 900. Circuitry (e.g., processing circuitry, an assessment circuit, etc.) is a collection of circuits implemented in tangible entities of the machine 900 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 900 follow.

In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine 900 (e.g., computer system) may include a hardware processor 902 (e.g., a central processing unit (CPU), a graphics processing unit (GPU), a hardware processor core, or any combination thereof), a main memory 904, a static memory 906 (e.g., memory or storage for firmware, microcode, a basic-input-output (BIOS), unified extensible firmware interface (UEFI), etc.), and mass storage 908 (e.g., hard drive, tape drive, flash storage, or other block devices) some or all of which may communicate with each other via an interlink 930 (e.g., bus). The machine 900 may further include a display unit 910, an input device 912 (e.g., a keyboard), and a user interface (UI) navigation device 914 (e.g., a mouse). In an example, the display unit 910, input device 912, and UI navigation device 914 may be a touch screen display. The machine 900 may additionally include a signal generation device 918 (e.g., a speaker), a network interface device 920, and one or more sensors 916, such as a global positioning system (GPS) sensor, compass, accelerometer, or one or more other sensors. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the hardware processor 902, the main memory 904, the static memory 906, or the mass storage 908 may be, or include, a machine-readable medium 922 on which is stored one or more sets of data structures or instructions 924 (e.g., software) embodying or utilized by any one or more of the techniques or functions described herein. The instructions 924 may also reside, completely or at least partially, within any of registers of the hardware processor 902, the main memory 904, the static memory 906, or the mass storage 908 during execution thereof by the machine 900. In an example, one or any combination of the hardware processor 902, the main memory 904, the static memory 906, or the mass storage 908 may constitute the machine-readable medium 922. While the machine-readable medium 922 is illustrated as a single medium, the term "machine-readable medium" may include a single medium or multiple media (e.g., a centralized or distributed database, and/or associated caches and servers) configured to store the one or more instructions 924.

The term "machine-readable medium" may include any medium that is capable of storing, encoding, or carrying instructions for execution by the machine 900 and that cause the machine 900 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 924 may be further transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 900, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical device system, comprising:

a stimulation circuit configured to generate first and second stimulation signals in different respective first and second stimulation modes, the first stimulation mode comprising cardiac resynchronization therapy (CRT) mode and the second stimulation mode comprising a multi-site pacing (MSP) mode, the first and second stimulation signals configured to be provided to a heart of a patient;

a signal receiver circuit configured to receive physiologic information of the patient, including thoracic impedance information and respiration information, the thoracic impedance information including intrathoracic impedance (ITTI) information and the respiration information including rapid shallow breathing index (RSBI) information; and an assessment circuit configured to control transition of the stimulation circuit between the first and second stimulation modes, including to:

determine, using physiologic information from a first time period when the stimulation circuit is in the first stimulation mode, a patient metric as a function of the ITTI information and the RSBI information indicative that the patient will respond to the second stimulation mode before the second stimulation mode is implemented; and control transition of the stimulation circuit from the first stimulation mode to the second stimulation mode based on the determined patient metric.

2. The system of claim 1, wherein the assessment circuit is configured to control implementation of the first stimulation mode at a first time, wherein the first time period occurs after the first time, and wherein to control transition of the stimulation circuit from the first stimulation mode to the second stimulation mode comprises at a second time after the first time period.

3. The system of claim 2, wherein to control transition of the stimulation circuit from the first stimulation mode to the second stimulation mode at the second time comprises to:

compare the determined patient metric to a threshold;

transition the stimulation circuit from the first stimulation mode to the second stimulation mode if the determined patient metric exceeds a first threshold; and retain the stimulation circuit in the first stimulation mode if the determined patient metric does not exceed the first threshold.

4. The system of claim 1, wherein the stimulation circuit is configured to generate stimulation signals to be delivered to at least one of a single electrode in a first chamber of the heart or a single electrode in a second chamber of the heart in the CRT mode, and wherein the stimulation circuit is configured to generate stimulation signals to be delivered to multiple electrodes in one of the first or second chambers of the heart in the MSP mode.

5. The system of claim 4, wherein, in the CRT mode, the stimulation circuit is configured to generate biventricular pacing signals to be delivered to a single electrode in each of a right and a left ventricle of the heart, and wherein, in the MSP mode, the stimulation circuit is configured to generate stimulation signals to be delivered to multiple electrodes in the left ventricle of the heart.

6. A method comprising:

generating, using a stimulation circuit, first and second stimulation signals in different respective first and second stimulation modes, the first stimulation mode comprising cardiac resynchronization therapy (CRT) mode and the second stimulation mode comprising a multi-site pacing (MSP) mode, the first and second stimulation signals configured to be provided to a heart of a patient;

receiving, using a signal receiver circuit, physiologic information of the patient, including thoracic impedance information and respiration information, the thoracic impedance information including intrathoracic impedance (ITTI) information and the respiration information including rapid shallow breathing index (RSBI) information; and controlling, using an assessment circuit, transition of the stimulation circuit between the first and second stimulation modes, including:

determining a patient metric indicative that the patient will respond to the second stimulation mode as a function of the ITTI information and the RSBI information from a first time period before the second stimulation mode is implemented; and controlling transition of the stimulation circuit from the first stimulation mode to the second stimulation mode based on the determined patient metric.

7. The method of claim 6, wherein the first time period occurs while the stimulation circuit is in the first stimulation mode.

8. The method of claim 7, comprising:

controlling implementation of the first stimulation mode at a first time, wherein the first time period occurs after the first time, wherein controlling transition of the stimulation circuit from the first stimulation mode to the second stimulation mode comprises at a second time after the first time period.

9. The method of claim 8, wherein controlling transition of the stimulation circuit from the first stimulation mode to the second stimulation mode at the second time comprises:

comparing the determined patient metric to a threshold;

transitioning the stimulation circuit from the first stimulation mode to the second stimulation mode if the determined patient metric exceeds a first threshold; and retaining the stimulation circuit in the first stimulation mode if the determined patient metric does not exceed the first threshold.

10. The method of claim 6, wherein the stimulation circuit is configured to generate stimulation signals to be delivered to at least one of a single electrode in a first chamber of the heart or a single electrode in a second chamber of the heart in the CRT mode, and wherein the stimulation circuit is configured to generate stimulation signals to be delivered to multiple electrodes in one of the first or second chambers of the heart in the MSP mode.

11. The method of claim 10, wherein, in the CRT mode, the stimulation circuit is configured to generate biventricular pacing signals to be delivered to a single electrode in each of a right and a left ventricle of the heart, and wherein, in the MSP mode, the stimulation circuit is configured to generate stimulation signals to be delivered to multiple electrodes in the left ventricle of the heart.

12. The medical device system of claim 1, wherein the RSBI information includes at least one of:

a power spectral density (PSD) peak width of the RSBI signal over the first time period;

a number of days during the first time period for which the RSBI exceeds a population mean; or a mean RSBI value determined over a terminal portion of the first time period preceding implementation of the second stimulation mode.

13. The medical device system of claim 1, wherein the ITTI information includes at least one of:

a modal value of the ITTI signal determined over the first time period;

a number of days during the first time period for which the ITTI exceeds a population mean; or a maximum real Fast Fourier Transform (FFT) spectral value of the ITTI signal over the first time period.

14. The medical device system of claim 1, wherein the signal receiver circuit is configured to receive heart sound information of the patient including a first heart sound (S1) parameter and a third heart sound (S3) parameter, wherein the assessment circuit is configured to determine, using physiologic information from before the first time period, prior to implementing the first stimulation mode or the second stimulation mode, a pre-stimulation patient metric as a function of the RSBI information and a ratio of the S3 parameter to the S1 parameter, the pre-stimulation patient metric indicative that the patient will respond to the first stimulation mode, and to control implementation of the first stimulation mode based on the determined pre-stimulation patient metric, wherein, after implementation of the first stimulation mode, the assessment circuit is configured to transition to determine the patient metric as the function of the ITTI information and the RSBI information and to control transition between the first and second stimulation modes based on the determined patient metric as the function of the ITTI information and the RSBI information.

15. The method of claim 6, wherein the RSBI information includes at least one of:

a power spectral density (PSD) peak width of the RSBI signal over the first time period;

a number of days during the first time period for which the RSBI exceeds a population mean; or a mean RSBI value determined over a terminal portion of the first time period preceding implementation of the second stimulation mode.

16. The method of claim 6, wherein the ITTI information includes at least one of:

a modal value of the ITTI signal determined over the first time period;

a number of days during the first time period for which the ITTI exceeds a population mean; or a maximum real Fast Fourier Transform (FFT) spectral value of the ITTI signal over the first time period.

17. A medical device system, comprising:

a stimulation circuit configured to generate first and second stimulation signals in different respective first and second stimulation modes, the first stimulation mode comprising cardiac resynchronization therapy (CRT) mode and the second stimulation mode comprising a multi-site pacing (MSP) mode, the first and second stimulation signals configured to be provided to a heart of a patient;

a signal receiver circuit configured to receive physiologic information of the patient, including thoracic impedance information and respiration information, the thoracic impedance information including intrathoracic impedance (ITTI) information and the respiration information including rapid shallow breathing index (RSBI) information; and an assessment circuit configured to control transition of the stimulation circuit between the first and second stimulation modes, including to:

determine, using physiologic information from a second time period when the stimulation circuit is in the second stimulation mode, a patient metric as a function of the ITTI information and the RSBI information indicative of insufficient patient response to the second stimulation mode; and control transition of the stimulation circuit from the second stimulation mode to the first stimulation mode based on the determined patient metric.

18. The system of claim 17, wherein to control transition of the stimulation circuit from the second stimulation mode to the first stimulation mode, the assessment circuit is configured to:

compare the determined patient metric to a threshold;

transition the stimulation circuit from the second stimulation mode to the first stimulation mode if the determined patient metric exceeds the threshold; and retain the stimulation circuit in the second stimulation mode if the determined patient metric does not exceed the threshold.

19. The system of claim 17, wherein the stimulation circuit is configured to generate biventricular pacing signals to be delivered to a single electrode in each of a right and a left ventricle of the heart in the CRT mode and to generate stimulation signals to be delivered to multiple electrodes in the left ventricle of the heart in the MSP mode.

20. The system of claim 17, wherein the RSBI information includes at least one of:

a power spectral density (PSD) peak width of the RSBI signal over the second time period;

a number of days during the second time period for which the RSBI exceeds a population mean; or a mean RSBI value determined over a terminal portion of the second time period, wherein the ITTI information includes at least one of:

a modal value of the ITTI signal determined over the second time period;

a number of days during the second time period for which the ITTI exceeds a population mean; or a maximum real Fast Fourier Transform (FFT) spectral value of the ITTI signal over the second time period.

* * * * *